United States Patent [19]

Hall et al.

[11] Patent Number: 4,866,270

[45] Date of Patent: Sep. 12, 1989

[54] METHOD AND APPARATUS FOR THE DETERMINATION OF ISOTOPIC COMPOSITION

[75] Inventors: Keith Hall, Altrincham; Philip A. Freedman, Hartford; Elizabeth J. Jumeau, Leftwich, all of England; Roger Guilluy, St Bonnet de Mure; Christiane Pachiaudi, Meyrieu, both of France

[73] Assignee: VG Instruments Group Limited, Crawley, England

[21] Appl. No.: 238,898

[22] Filed: Aug. 31, 1988

[30] Foreign Application Priority Data

Sep. 2, 1987 [GB] United Kingdom ............... 8720586
May 13, 1988 [GB] United Kingdom ............... 8811379

[51] Int. Cl.$^4$ .................................................. H01J 49/04
[52] U.S. Cl. .................................. 250/282; 250/288; 436/173
[58] Field of Search .................... 250/282, 288, 288 A; 436/173

[56] References Cited

U.S. PATENT DOCUMENTS 4,207,465  6/1980  Favre et al. .................... 250/288
4,495,414  1/1985  Barrie et al. .................... 250/288

OTHER PUBLICATIONS

D. A. Schoeller and J. M. Hays, Computer Controlled Ion Counting Isotope Ratio Mass Spectrometer, Analytical Chemistry 1975 47(3), 408–414.
D. E. Matthews and J. M. Hays, Isotope-Ratio-Monitoring Gas Chromatography Mass Spectrometry Analytical Chemistry 1978, 50 (11), 1465–1473.
A. Barrie, J. Bricout and J. Koziet, Gas Chromatography—Stable Isotope Ration Analysis at Natural Abundance Levels, Biomedical Mass Spectrometry, 1984, 11(11) 583–588.
T. Preston and N. J. P. Owens, Interfacing on Automatic Elemental Analyzer with an Isotope Ratio Mass Spectrometer Analyst, 1983, 108, 971–977.

*Primary Examiner*—Jack I. Berman
*Attorney, Agent, or Firm*—Chilton, Alix & Van Kirk

[57] ABSTRACT

The invention comprises methods and apparatus for the mass spectrometric determination of the isotopic composition of an element comprised in an analysis gas (that is, a gas comprising the element in elemental form or in the form of a simple compound, e.g., nitrogen or carbon dioxide). First and second flows of a carrier gas (e.g., helium) are simultaneously passed into the mass spectrometer, and samples of analysis gas and a reference gas are respectively introduced into the first and second flows during selected time intervals. The time intervals are selected so that mass spectrometric measurements are made on the analysis gas samples in the absence of any signal from the reference gas samples, and v.v. A preferred embodiment comprises a gas chroatograph through which a sample containing the element is passed, and conversion means to convert the eluting sample into the analysis gas.

22 Claims, 2 Drawing Sheets

METHOD AND APPARATUS FOR THE DETERMINATION OF ISOTOPIC COMPOSITION

This invention relates to a mass spectrometer for determining the isotopic composition of an element comprised in a gaseous sample, and to methods and apparatus for introducing samples into such a spectrometer.

The isotopic composition of an element such as carbon, nitrogen or sulphur may be determined by converting a sample comprising the element into an analysis gas, (that is, a gas comprising the element in either elemental form or in the form of a simple compound, eg carbon dioxide, nitrogen or sulphur dioxide), and determining the isotopic composition of the analysis gas using a multiple collector isotope ratio mass spectrometer equipped with a suitable gas inlet system.

Suitable inlet systems typically comprise a changeover valve which selects as required either the analysis gas or a reference gas and admits it to the ion source of the mass spectrometer via a viscous leak. Adjustable volume reservoirs are provided on both the analysis gas inlet and the reference inlet so that the pressure of the analysis gas and a reference gas can be brought to predetermined values. The analysis gas is typically collected and stored in transfer vessels fitted with a valve, and the analysis gas inlet of the spectrometer is fitted with a manifold to which approximately ten transfer vessels can be fitted. A computer is used to control the spectrometer and the inlet system so that the samples of analysis gas can be analyzed automatically one after the other, without operator intervention.

Inlet systems of this type work well when a large amount of analysis gas is available, but are unsatisfactory with small quantities of analysis gas. When the analysis gas is carbon dioxide, small samples are better analyzed by freezing the carbon dioxide into a low-volume cold trap and subsequently vaporizing it into a smaller volume in the inlet system, thereby increasing its pressure sufficiently to allow an accurate analysis. Cold traps are provided as standard features of the inlet system on mant spectrometers, and it is known to automate their operation.

An alternative method of analyzing small volumes of analysis gas is to dilute the samples with helium, as described by Schoeller and Hayes (Analytical Chemistry, 1975, vol. 47(3) pp 408–414). The carbon dioxide is vaporized, and the resultant helium-carbon dioxide mixture is admitted into the spectrometer using the conventional adjustable volume reservoirs. The reference sample is treated in a similar way. This method has not been adopted as standard practice, however.

The sample introdudction methods so far described are batch processes involving the adjustment of the pressure in the inlet to a particular value before the analysis is started, and the use of a changeover valve to switch between the analysis gas and a reference gas as required.

Continuous flow sample introduction methods for use with a gas chromatograph or an elemental analyzer are also known, but up to now have lacked the precision obtainable from the conventional batch inlet systems. See, for example, Matthews and Hayes, Analytical Chemistry, 1978, vol.50(11) pp 1465–1473, Barrie, Bricout and Koziet, Biomedical Mass Spectrom, 1984, vol.11(11) pp 583–588, and Preston and Owens, Analyst, 1983, vol.108 pp 971–977.

A need therefore exists for an inlet system which is capable of faster operation than the known batch inlet systems but which allows the precision obtainable with these systems.

It is an object of the invention to provide a method of, and apparatus for, introducing samples into a gas-analyzing isotope ratio mass spectrometer and for calibrating the same. It is further object to provide a method of improved accuracy for interfacing a gas chromatograph/combustion furnace or an elemental analyzer to a mass spectrometer.

In accordance with this objective the invention provides a method of determining the isotopic composition of an element comprised in an analysis gas (that is, a gas comprising said element in elemental form or in the form of a simple compound, eg, nitrogen or carbon dioxide), said method comprising the steps of:

(a) passing simultaneously at least a first and a second flowa of a carrier gas into a mass spectromether arranged for the determination of the isotopic composition of said analysis gas;

(b) introducing during at least one first time interval a sample of said analysis gas into said first flow;

(c) introducing during at least one second time interval a sample of reference gas into said second flow;

(d) determining the isotopic composition of said element in said sample from the outputs of said mass spectrometer during mass analyses of said analysis gas and said reference gas; and (e) selecting said first and second time intervals so that during any period when a mass analysis of said analysis gas is being carried out, there is substantially no output of said mass spectrometer indicative of said element in said reference gas, and so that during any period when a mass analysis of said reference gas is being carried out, there is substantially no output of said mass spectrometer indicative of said element in said analysis gas.

In a preferred embodiment the method of the invention comprises a method for the determination of the isotopic composition of an element comprised in a sample, said method comprising:

(a) passing a first flow of a carrier gas through a gas chromatographic column and introducing said sample on to said column;

(b) converting at least some of said sample after it has passed through said column into an analysis gas (that is a gas comprising said element in elemental form or in the form of a simple compound, eg, nitrogen or carbon dioxide) so that said analysis gas is present in said first flow of a carrier gas for at least one first time interval;

(c) introducing at least some of said first flow of carrier gas and analysis gas into an isotope ratio mass spectrometer arranged for the determination of the isotopic composition of said element in said analysis gas;

(d) introducing into said mass spectrometer simultaneously with said first flow of carrier gas and analysis gas a second flow of a carrier gas;

(e) introducing a sample of a reference gas into said second flow of a carrier gas so that said reference gas is present in said second flow for at least one second time interval;

(f) monitoring the outputs of said mass spectrometer indicative of particular isotopes of said element in both said analysis gas and said reference gas, and determining the isotopic composition of said element in said analysis gas therefrom; and (g) selecting said first and second time intervals so that during any period when the output of said mass spectrometer indicative of said element in said analysis gas is monitored, there is substantially no output due to any sample of said reference gas, and so that during any period in which the output of said mass spectrometer indicative of said element in said reference gas is monitored, there is substantially no output due to any sample of said analysis gas.

Preferably the first and second flows are introduced into the ion source of the mass spectrometer through separate viscous leaks. Alternatively, the flows may be mixed and introduced through a single viscous leak.

Preferably also the carrier gas is helium. The samples of analysis gas and reference gas may be introduced into the first and second flows by means for example of conventional GC sample valves or alternatively by injection from suitable gas-tight syringes through septa fitted on the lines carrying the first and second flows of carrier gas.

Preferably the mass spectrometer is provided with means for integrating each output indicative of a particular isotope, and the integration is carried out over the period during which signals from at least the analysis gas and preferably the reference gas, are present. In some circumstances, it may be preferable to start the integration period when the output reaches a certain predetermined level, and to finish it when the signal falls below a second predetermined level, but in general integration over substantially all of the periods in which the reference gas or analysis gas enters the mass spectrometer is preferred.

In a further preferred embodiment at least the first flow of a carrier gas is arranged to be substantially greater than that required by the mass spectrometer, and the excess flow is vented at a substantially constant, eg, atmospheric, pressure through an open split located downstream of the point at which the analysis gas is introduced. A similar arrangement may be adopted for the second flow of a carrier gas into which the reference gas is introduced.

Viewed from another aspect the invention provides apparatus for the determination of the isotopic composition of an element comprised in an analysis gas (that is, a gas comprising said element in elemental form or in the form of a simple compound, eg, nitrogen or carbon dioxide), said apparatus comprising:

(a) a mass spectrometer arranged for the determination of the isotopic composition of said element in said analysis gas;

(b) first duct means for carrying a first flow of a carrier gas;

(c) second duct means for carrying a second flow of a carrier gas;

(d) inlet means for admitting into said mass spectrometer gas from said first and from said second duct means;

(e) first sample introduction means operable during first selected time intervals to introduce samples of said analysis gas into said first duct means;

(f) second sample introduction means operable during second selected time intervals to introduce samples of a reference gas into said seocnd duct means;

in which said first and second time intervals are selected so that said mass spectrometer may generate signals indicative of said element in said analysis gas subtantially free from signal contributions due to said element in said reference gas and may generate signals indicative of said element in said reference gas substantially free from signal csontributions due to said element in said analysis gas.

A preferred embodiment of the apparatus of the invention thus comprises apparatus for the determination of the isotopic composition of an element comprised in a sample, said apparatus comprising:

(a) a gas chromatographic column through which a said sample may be passed in a first flow of a carrier gas;

(b) sample conversion means disposed to receive at least a part of the effluent of said column and arranged to convert a said sample into an analysis gas (that is, a gas comprising said element in elemental form or in the form of a simple compound, eg, nitrogen or carbon dioxide);

(c) isotopic-ratio mass spectrometer arranged for the determination of the isotopic composition of said element in a sample of said analysis gas and disposed to receive at least some of the effluent from said conversion means;

(d) means for introducing a second flow of a carrier gas into said mass spectrometer, simultaneously with said first flow;

(e) means for introducing a reference gas into said second flow, said means operable during time intervals selected so that said mass spectrometer may generate signals indicative of said element in said analysis gas substantially free from signal contributions due to said element in said reference gas and generate signals indicative of said element in said reference gas substantially free from signal contributions due to said element in said analysis gas; and (f) means for determining the isotopic composition of said element comprised in said sample from signals generated by said mass spectrometer in the mass analyses of said analysis gas and said reference gas.

Preferably either or both the first and second flows of carrier gas are substantially greater than that required by the mass spectrometer, and open split means are provided to discharge the excess flow to a substantially constant eg, atmospheric, pressure. Preferably also the carrier gas is helium. In the case when the isotopic composition of carbon is to be determined, the analysis gas and reference gas are preferably carbon dioxide, and trapping means may be provided to remove water and other condensable impurities form the flow of carrier gas and analysis gas before it is admitted to the mass spectrometer. The trapping means preferably comprises a cold trap maintained at a temperature sufficiently low to freeze the water but high enough to avoid condensing the analysis gas.

Preferred embodiments of the invention will now be described in detail and by reference to the figures, in which.

Figure 1:
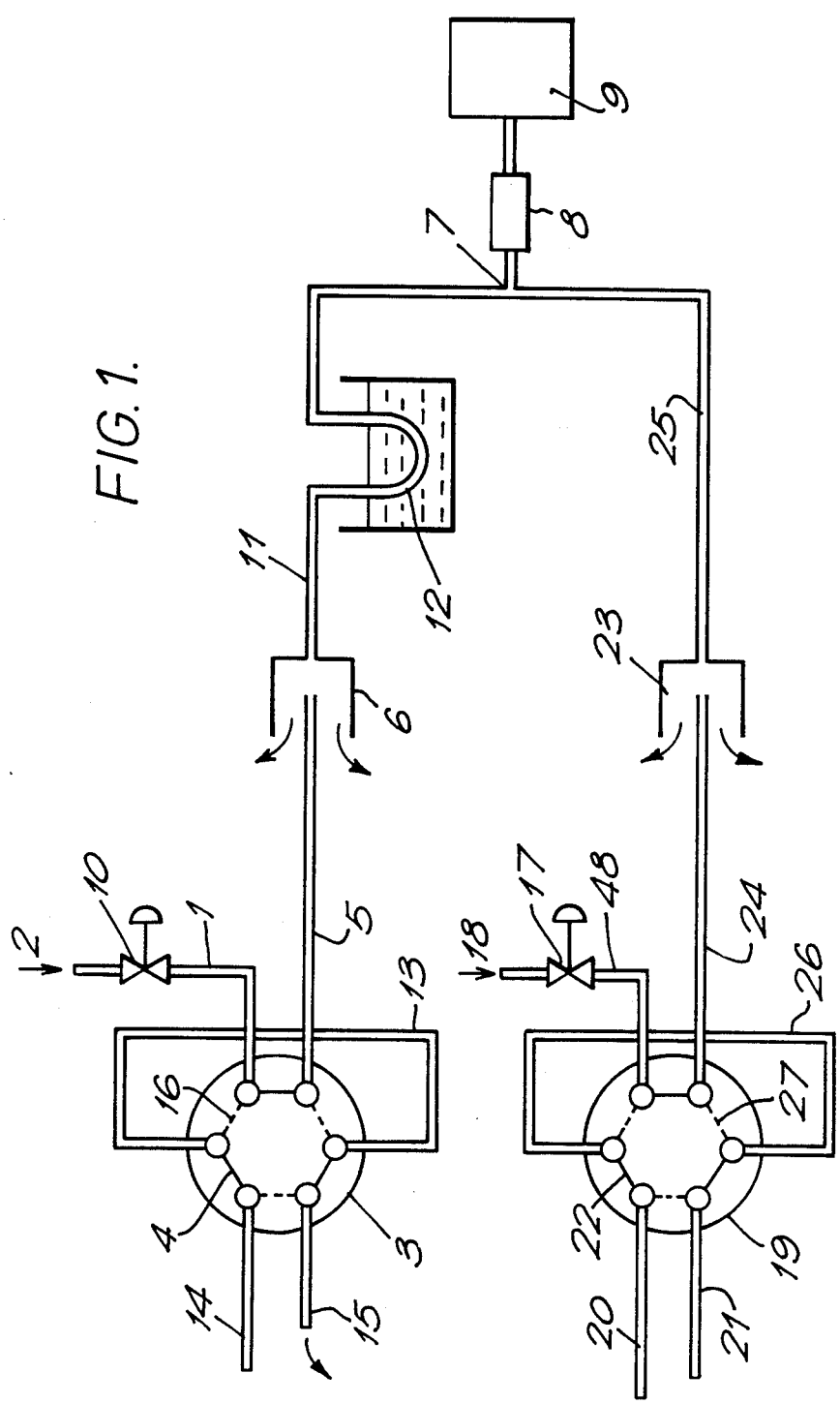
FIG. 1 is a schematic drawing of an apparatus according to the invention.

Referring first to FIG. 1, a first flow of carrier gas (typically helium) is introduced through a flow regulator 10 into first duct means comprising pipe 1 in the direction of arrow 2, conveniently at 20-30 ml. $min^{-1}$. Pipe 1 is connected to one inlet port of conventional six-port sampling valve 3, as shown. When valve 3 is in the position indicated by the solid lines 4, the inert gas passes out of valve 3 via pipe 5 into an open split 6 which discharges excess carrier gas at atmospheric presssure. A small portion (approximately 0.2 ml. $min^{-1}$) of the gas passes from the split 6 into pipe 11 and passes through a trap 12 maintained at a temperature low enough to freeze any water present in the gas but above the temperature at which the analysis gas (see below) would be condensed. The gas then flows via 'T' connector 7 through a viscous restrictor 8 into the ion source of a multiple collector isotope ratio mass spectrometer 9.

A sample of the analysis gas comprising the element whose isotopic composition is to be determined, eg gaseous nitrogen in the case of the determination of $^{14}N$ and $_{15}N$ or carbon dioxide in the case of the determination of $^{12}C$ and $^{13}C$, is caused to flow through a sample loop 13 on valve 3 via the analysis gas inlet pipe 14 and subsequently to vent pipe 15 while valve 3 is in the position indicated by the solid lines 4. In order to introduce a sample of the analysis gas into the first flow of carrier gas, valve 3 is turned so that the ports are connected via the dotted lines 16 so that the first flow of carrier gas is diverted through the sample loop 13, which carries a sample of the analysis gas into pipe 5 and subsequently into the mass spectrometer 9.

A very similar arrangement comprising a flow regulator 17, second conventional 6-port sample valve 19 and sample loop 26 provides a means for introducing a sample of reference gas into a second flow of carrier gas which flows through regulator 17 and second duct means comprising pipe 48 in the direction of arrow 18. When valve 19 is in the position shown by the solid lines 22, the second flow of carrier gas flows via pipe 24 to a second open split 23, similar to the open split 6, and subsequently through pipe 25 to 'T' connector 7 where it is mixed with the first flow of carrier gas. Reference gas (of the same chemical composition as the analysis gas) flows from the reference gas inlet 20 through sample loop 26 and leaves the valve through the reference gas vent 21. Rotation of valve 19 connects the ports as indicated by the dotted lines 27, thereby introducing a sample of the reference gas into the second flow of carrier gas.

According to the invention, valve 3 is operated during a first time interval to admit a sample of analysis gas into mass spectrometer 9. The output singal(s) from the mass spectrometer which are indicative of the element to be analyzed (eg m/e ratios 44, 45 and 46 in the case of carbon, for which the analysis gas comprises carbon dioxide) are integrated over a period which starts when the signal exceeds a first predetermined threshold and terminates when the signal falls below a second predetermined threshold. When there is substantially no output signal(s) due to the analysis gas introduced in the first time interval, valve 19 is operated for a second time interval to introduce a sample of reference gas into the second flow of carrier gas, and the output signal(s) are again integrated. Another sample of analysis gas may be introduced using valve 3 once there is substantially no output signal(s) due to the sample introduced in the second time interval. This process may be repeated as often as necessary to obtain the desired accuracy of ratio measurement, in the manner of conventional isotope ratio mass spectrometry, and the isotopic composition calculated from the ratio measurements made, again in a conventional manner.

Preferably, the outputs of the mass spectrometer are integrated with respect to time during the periods in which the analysis gas and the reference gas are entering the mass spectrometer, so that the data acquisition system conventionally comprised in mass spectrometer 9 includes means for integrating the output signals. In this way the effect of any fractionation of the analysis gas or reference gas in any part of the inlet system, particularly significant when a gas chromatograph is included, can be minimized. Further preferably the integration is carried out for substantially all of the time the analysis gas or the reference gas enters the spectrometer 9.

It has been found that use of a dual dynamic inlet system of the type described results in a precision approaching that achievable with a conventional batch inlet system.

Use of the method and apparatus of the invention results in a considerable saving of time in running samples and elimination of the highly critical and expensive changeover valve which is an essential part of prior conventional inlet systems.

It will be appreciated that the 6-port sample valves 3 and 19 could be replaced by any suitable means for introducing a sample of the analysis gas or reference gas into the carrier gas flows. For example, an injection port may be fitted between pipes 1 and 5 and a sample of analysis gas injected into the first flow of inert gas from a suitable syringe. Alternatively, a more uniformly mixed flow of analysis gas and carrier gas may be formed by slowly introducing a sample of analysis gas into the carrier gas in a controlled way.

Figure 2:
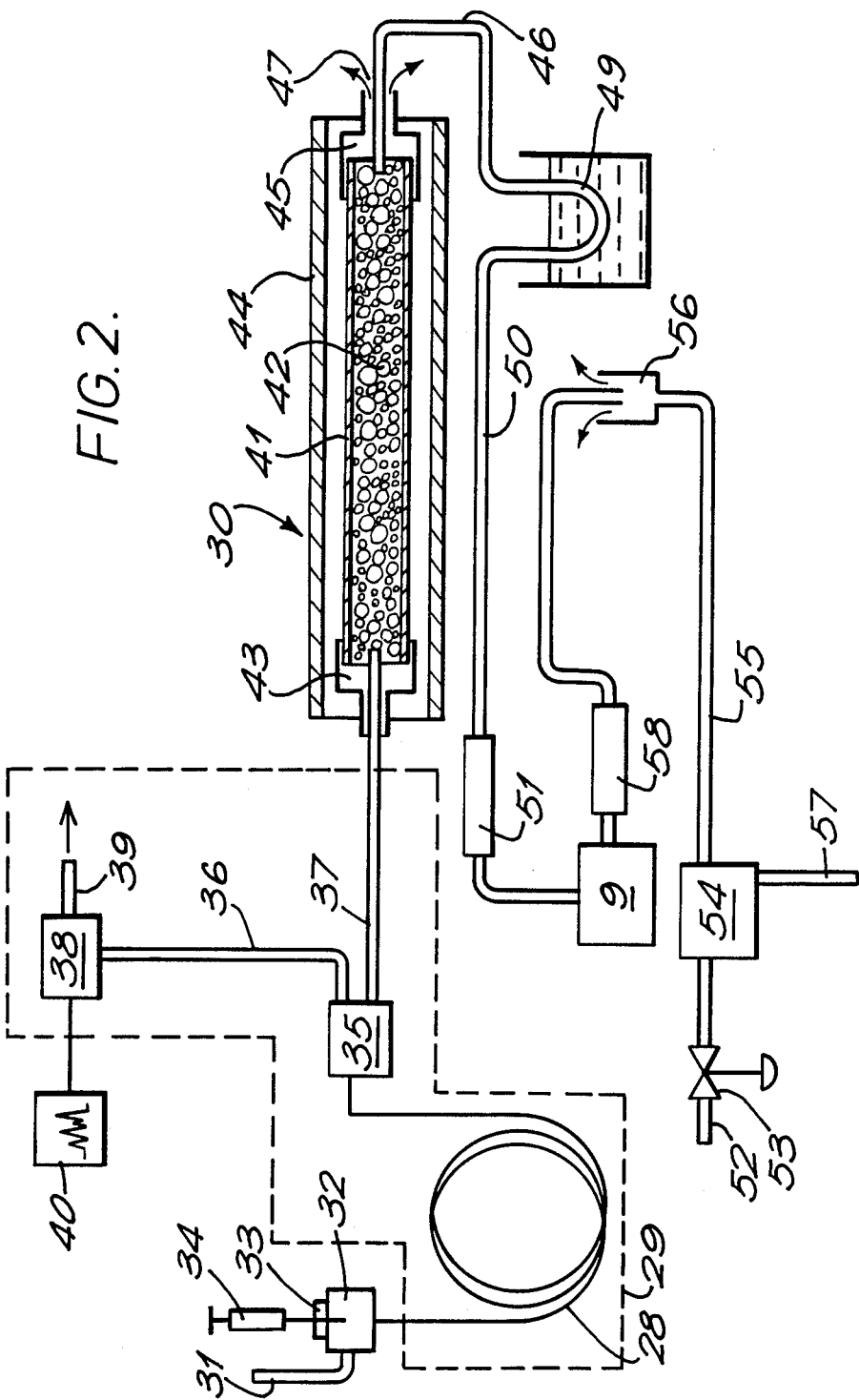
FIG. 2 is a schematic drawing of a further apparatus according to the invention.

Referring next to FIG. 2 a combined gas chromatograph-isotope ratio mass spectrometer for the determination of carbon isotopic ratios comprises a gas chromatographic column 28 enclosed in a temperature controlled oven indicated by 29, and a sample conversion means which comprises a combustion furnace 30 adapted for oxidizing a carbon-containing sample to carbon dioxide. A first flow of carrier gas enters column 28 through an inlet 31 and an injection port 32. A sample for which the carbon isotopic composition is to be determined (or a mixture containing it) is injected from a syringe 34 through a septum 33 on the injection port 32 into the first flow of carrier gas. The effluent from column 28 enters a split 35 located in oven 29 which divides it into two portions. One portion leaves through pipe 36 and passes into a flame-ionization detector 38, subsequently venting to atmosphere through vent 39, and the other portion leaves the oven 29 through pipe 37 and enters the combustion furnace 30. The flame-ionization detector 38 is connected to an amplifier and recorder 40, allowing a gas chromatorgram of the injected sample to be recorded.

Combustion furnace 30 comprises a quartz tube 41, typically 0.5 mm inside diameter by 30 cm long, which is packed with cupric oxide or cobaltic oxide (CuO or $Co_3O_4$) granules 42 of 0.3-0.4 mm diameter. Pipe 37 is connected to tube 41 by a reducing coupling 43. Tube 41 is heated by an electrically heated furnace 44 which surrounds it as shown. The temperature of tube 41 is maintained typically at 700°-900° C.

Effluent emerging from tube 41, now comprising the analysis gas (carbon dioxide) in helium carrier gas passes through a reducing coupling 45 into pipe 46. An open split 47 is conveniently provided by ensuring that the inside diameter of the coupling 45 is greater than the outside diameter of pipe 46, as shown. A small portion of the flow of analysis gas and carrier gas leaves the tube 41 in pipe 46 and enters cold trap 49.

Split 47 and trap 49 are equivalent to the split 6 and trap 12 of the embodiment shown in FIG. 1 and need not be described in further detail.

After passing through the trap 49, the first flow of carrier gas passes via pipe 50 and a viscous restrictor 51 into the mass spectrometer 9, as in the FIG. 1 embodiment.

According to the invention, a second flow of carrier gas enters through inlet 52 through a flow regulator 53 and into a sampling valve schematically shown by 54. Sampling valve 54 is constructed in the same manner as the arangement of the six-port valve 19, sampling loop 26 and the associated components of the FIG. 1 embodiment, and provides means for introducing a sample of reference gas introduced into inlet 57 into the second flow of carrier gas during a particular time interval. Also in the same manner as the FIG. 1 embodiment, the second flow of carrier gas leaves sampling valve 54 via pipe 55 and another open split 56 and is introduced into the mass spectrometer 9 through a second viscous restrictor 58. Split 56 serves the same function as split 23 of the FIG. 1 embodiment.

Alternatively, sampling valve 54 may be replaced by a gas mixing arangement which allows the reference gas to be mixed with the second flow of carrier gas during a predetermined time interval. Such arrangements are well known in the art.

In operation, a sample mixture containing components whose isotopic composition is to be determined is injected from syringe 34 and is separated by the chromatographic column 28 as in a conventional chromatograph. As each component of the mixture elutes, the carbon it contains is oxidized to carbon dioxide by the combustion furnace 30, and condensable material is subsequently removed by the cold trap 49, so that the gas in pipe 50 comprises the first flow of carrier gas in which is present a series of "peaks" comprising carbon dioxide, corresponding to the orginial components of the mixture. These "peaks" are isotopically analyzed by the spectrometer to determine the $^{13}C/^{12}C$ ratios characteristic of each of the original materials. The reference gas is introduced into a second flow of carrier gas by the sampling valve 54 and this is introduced through the second viscous leak 58 into the spectrometer according to the invention. (A single viscous leak and one inlet to the mass spectrometer 9 may be provided if desired). Consequently, the analysis gas is introduced into the first flow of carrier gas during a first time interval which corresponds to the time that any one of the "oxidized GC peaks" is present in the first flow of carrier gas. Sampling valve 54 is then operated during the intervals between the peaks to introduce reference gas into the second flow of carrier gas during times when there is no signal from the mass spectrometer due to the oxidized GC peaks in the first flow. In this way the precision of the isotopic ratio measurements can be increased in comparison with prior isotope-ratio mass spectrometer/gas chromatographic apparatus and methods.

It will also be appreciated that the apparatus and method of the invention can be adapted for use with an elemental analyzer in place of the gas chromatograph. It will be further appreciated that the FIG. 2 embodiment of the invention can be simply adapted for the determination of other elements (eg nitrogen or sulphur) by replacing the combustion furnace 30 with other sample conversion means designed to convert, for example, the elemental nitrogen or sulphur present in a sample to nitrogen gas or sulphur dioxide, respectively.

What is claimed is:

1. A method of determining the isotopic composition of an element comprised in an analysis gas (that is, a gas comprising said element in elemental form or in the form of a simple compound said method comprising the steps of:
   (a) passing simultaneously at least a first and a second flow of a carrier gas into a mass spectrometer arranged for the determination of the isotopic composition of said analysis gas;
   (b) introducing during at least one first time interval a sample of said analysis gas into said first flow;
   (c) introducing during at least one second time interval a sample of reference gas into said second flow;
   (d) determining the isotopic composition of said element in said sample from the outputs of said mass spectrometer during mass analysis of said analysis gas and said reference gas; and
   (e) selecting said first and second time intervals so that during any period when a mass analysis of said analysis gas is being carried out, there is substantially no output of said mass spectrometer indicative of said element in said reference gas, and so that during any period when a mass analysis of said reference gas is being carried out, there is substantially no output of said mass spectrometer indicative of said element in said analysis gas.

2. A method according to claim 1 in which said first and second flows are introduced into said mass spectrometer through separate viscous leaks.

3. A method according to claim 1 in including the additional step of integrating with respect to time at least some of the outputs of said mass spectrometer during mass analyses of said analysis gas which are indicative of particular isotopes of said element for substantially all of the time they are present.

4. A method according to claim 1 in which at least said first flow of a carrier gas is substantially greater than that required by said mass spectrometer and the excess flow is vented at a substantially constant pressure downstream of the point at which said analysis gas is introduced.

5. A method for the determination of the isotopic composition of an element comprised in a sample, said method comprising:
   (a) passing a first flow of a carrier gas through a gas chromatographic column and introducing said sample on to said column;
   (b) converting at least some of said sample after it has passed through said column into an analysis gas (that is a gas comprising said element in elemental form or in the form of a simple compound so that said analysis gas is present in said first flow of a carrier gas for at least one first time interval;
   (c) introducing at least some of said first flow of carrier gas and analysis gas into an isotope ratio mass spectrometer arranged for the determination of the isotopic composition of said element in said analysis gas;
   (d) introducing into said mass spectrometer simultaneously with said first flow of carrier gas and analysis gas a second flow of a carrier gas;
   (e) introducing a sample of a reference gas into said second flow of a carrier gas so that said reference gas is present in said second flow for at least one second time interval;
   (f) monitoring the outputs of said mass spectrometer indicative of particular isotopes of said element in both said analysis gas and said reference gas, and determining the isotopic composition of said element in said analysis gas therefrom; and (g) selecting said first and second time intervals so that during any period when the output of said mass spectrometer indicative of said element in said analysis gas is monitored, there is substantially no output due to any sample of said reference gas, and so that during any period in which the output of said mass spectrometer indicative of said element in said reference gas is monitored, there is substnatially no output due to any sample of said analysis gas.

6. A method according to claim 5 in which said first and second flows are introduced into said mass spectrometer through separate viscous leaks.

7. A method according to claim 5 including the additional step of integrating with respect to time at least some of the outputs of said mass spectrometer during mass analyses of said analysis gas which are indicative of particular isotopes of said element for substantially all of the time they are present.

8. A method according to claim 5 in which at least said flow of a carrier gas is substantially greater than that required by said mass spectrometer, in which the excess flow is vented at a substantially constant pressure downstream of the point at which said analysis gas is introduced.

9. Apparatus for the determination of the isotopic compositon of an element comprised in an analysis gas (that is, a gas comprising said element in elemental form or in the form of a simple compound, said apparatus comprising:

(a) a mass spectrometer arranged for the determination of the isotopic composition of said element in said analysis gas;

(b) first duct means for carrying a first flow of a carrier gas;

(c) second duct means for carrying a second flow of a carrier gas;

(d) inlet means for simultaneously admitting into said spectromete gas from said first and from said second duct means;

(e) first sample introduction means operable during first selected time intervals to introduce samples of said analysis gas into said first duct means;

(f) second sample introduction means operable during second selected time intervals to introduce samples of a reference gas into said second duct means;

in which said first and second time intervals are selected so that said mass spectrometer may generate signals indicative of said element in said analysis gas substantially free from signal contributions due to said element in said reference gas and may generate signals indicative of said element in said reference gas substantially free from signal contributions due to said element in said analysis gas.

10. Apparatus according to claim 9 in which said inlet means comprises two separate viscous leaks, one through which said first flow of a carrier gas is introduced and the other through which said second flow of a carrier gas is introduced.

11. Apparatus according to claim 9 further comprising means for integrating with respect to time the signals from said mass spectrometer indicative of at least one isotope of said element for substantially all of at least one period during which said analysis gas is entering said mass spectrometer.

12. A mass spectrometer according to claim 11 further comprising means for integrating with respect to time the signals from said mass spectrometer indicative of at least one isotope of said element during at least one period during which said reference gas is entering said mass spectrometer.

13. Apparatus according to claim 9 in which said first flow of a carrier gas is substantially greater than that required by said mass spectrometer, and open split means are provided to discharge the excess flow to a substantially constant pressure.

14. Apparatus according to claim 9 in which said second flow of a carrier gas is substantially greater than that required by said mass spectrometer and open split means are provided to discharge the excess flow to a substantially constant pressure.

15. Apparatus according to claim 9 in which the element whose isotopic composition is to be determined is carbon, said analysis gas and said reference gas comprise carbon dioxide, said carrier gas comprises helium and trapping means are provided to remove water and other condensable impurities from at least said first flow of carrier gas (and analysis gas, when present) before it enters said mass spectrometer.

16. Apparatus for the determination of the isotopic composition of an element comprised in a sample, said apparatus comprising:

(a) a gas chromatographic column through which a said sample may be passed in a first flow of a carrier gas;

(b) sample conversion means disposed to receive at least a part of the effluent of said column and arranged to convert a said sample into an analysis gas (that is, a gas comprising said element in elemental form or in the form of a simple compound);

(c) an isotopic-ratio mass spectrometer arranged for the determination of the isotopic composition of said element in a sample of said analysis gas and disposed to receive at least some of the effluent from said conversion means;

(d) means for introducing a second flow of a carrier gas into said mass spectrometer, simultaneously with said first flow;

(e) means for introducing a reference gas into said second flow, said means operable during time intervals selected so that said mass spectrometer may generate signals indicative of said element in said analysis gas substantially free from signal contributions due to said element in said reference gas and generate signals indicative of said element in said reference gas subbstantially free from signal contributions due to said element in said analysis gas; and (f) means for determining the isotopic composition of said element comprised in said sample from signals generated by said mass spectrometer in the mass analyses of said analysis gas and said reference gas.

17. Apparatus according to claim 16 in which said effluent from said conversion means is introduced into said mass spectrometer through a first viscous leak and said second flow of a carrier gas is introduced into said mass spectrometer through a second viscous leak.

18. Apparatus according to claim 16 in which said means for determining the isotopic composition comprise means for integrating with respect to time the signals from said mass spectrometer indicative of at least one isotope of said element for substantially all of at least one period during which said analysis gas is entering said mass spectrometer.

19. Apparatus according to claim 18 in which said means for determining the isotopic composition further comprise means for integrating with respect to time the signals from said mass spectrometer indicative of at least one isotope of said element for substantially all of at least one period during which said reference gas is entering said mass spectrometer.

20. Apparatus according to claim 16 in which the flow of effluent from said chromatographic column is substantially greater than that required by said mass spectrometer, and open split means are provided to discharge the excess flow to a substantially constant pressure.

21. Apparatus according to claim 16 in which said second flow of carrier gas is substantially greater than that required by said mass spectrometer, and open split means are provided to discharge the excess flow to a substantially constant pressure.

22. Apparatus according to claim 16 in which the element whose isotopic composition is to be determined is carbon, said analysis gas and said reference gas comprise carbon dioxide, said carrier gas comprises helium, and trapping means are provided to remove water and other condensable impurities from said effluent from said chromatographic column before it enters said mass spectrometer.

* * * * *